United States Patent [19]

Baggiolini et al.

[11] 4,026,882

[45] May 31, 1977

[54] SYNTHESES OF 3,24R,25- AND 3,24S,25-TRIHYDROXY-5,7-CHOLESTADIENE 24,25-KETALS AND ALKANOYL DERIVATIVES THEREOF

[75] Inventors: Enrico Baggiolini, Nutley; John Joseph Partridge, Jr.; Milan Radoje Uskokovic, both of Upper Montclair, all of N.J.

[73] Assignee: Hoffmann-La Roche Inc., Nutley, N.J.

[22] Filed: Mar. 8, 1976

[21] Appl. No.: 664,848

[52] U.S. Cl. .................. 260/239.55 D; 260/397.2
[51] Int. Cl.² ..................................... C07J 71/00
[58] Field of Search ............... 260/239.55 D, 397.2

[56] References Cited

UNITED STATES PATENTS

| 3,629,242 | 12/1971 | Fried | 260/239.55 D |
| 3,726,864 | 4/1973 | Phillipps et al. | 260/239.55 D |

*Primary Examiner*—Elbert L. Roberts
*Attorney, Agent, or Firm*—Samuel L. Welt; George M. Gould; Raymond R. Wittekind

[57] ABSTRACT

Syntheses of 3,24R,25- and 3,24S,25-trihydroxy-5,7-cholestadiene 24,25-ketals and alkanoyl derivatives thereof, intermediates in the preparation of the biologically important metabolite and derivative, respectively, of vitamin $D_3$, are described.

25 Claims, No Drawings

SYNTHESES OF 3,24R,25- AND 3,24S,25-TRIHYDROXY-5,7-CHOLESTADIENE 24,25-KETALS AND ALKANOYL DERIVATIVES THEREOF

BACKGROUND OF THE INVENTION

The isolation and characterization of 24,25-dihydroxycholecalciferol (24,25-dihydroxyvitamin $D_3$) (M. F. Holick et al., Biochemistry, 11, 4251 (1972)), and the subsequent finding that this second most abundant metabolite of vitamin $D_3$) (J. L. Omdahl and H. F. DeLuca, Physiological Reviews, 53, 327 (1973)) preferentially stimulates intestinal calcium transport without, at comparable dose levels, mobilizing bone calcium, prompted extensive investigation of the physiological role played by this metabolite (see for example, H. K. Schnoes and H. F. DeLuca, Vitamins and Hormones, 32, 395 (1974)). These investigations have been hampered by the minute amounts of the metabolite available from natural sources, the lack of information concerning the stereochemistry of the metabolic hydroxyl group at C-24 and the effect of the configuration of this group on the biological activity exhibited by 24,25-dihydroxycholecalciferol.

In 1973, M. Seki, et al., Chem. Pharm. Bull. (Japan), 21, 2783 (1973) described the conversion of desmosterol acetate to 24$\xi$,25-dihydroxycholesterol, a precursor of 24,25-dihydroxycholecalciferol. Shortly thereafter, H.-Y. Lam, et al., Biochemistry, 12, 4851 (1973) and J. Redel, et al., Compt. rend. Acad. Soc. (Paris), 278, 529 (1974) disclosed syntheses of 24$\xi$,25-dihydroxycholecalciferol starting from 3$\beta$-acetoxy-27-nor-5-cholesten-25-one and desmosterol acetate, respectively. These syntheses are non-stereospecific yielding mixtures of stereoisomers at C-24. M. Seki, et al., Tetrahedron Letters, 15 (1975) recently described the separation of 24$\xi$,25-dihydroxycholesterol into the 24R- and 25S-isomers and the conversion of the 24R- and 25S-isomers into 24R,25- and 24S,25-dihydroxycholecalciferol, respectively. This synthesis suffers from the inherent disadvantages associated with the separation step. Thus, stereospecific syntheses of 24R,25- and 24S,25-dihydroxycholecalciferol utilizing 24,25-dihydroxycholesterol derivatives of known stereochemistry at C-24 overcoming the deficiencies of the prior art processes and making this important metabolite of vitamin $D_3$ readily available for biological, clinical and therapeutic use would represent an important contribution to the advancement of the state of the art in the vitamin D field.

DETAILED DESCRIPTION OF THE INVENTION

The present invention relates to novel efficient processes for the preparation of 3,24R,25- and 3,24S,25-trihydroxy-5,7-cholestadiene 24,25-ketals and alkanoyl derivatives thereof starting from precursors readily available from natural sources. More particularly, the present invention relates to methods of synthesizing 3,24R,25- and 3,24S,25-trihydroxy-5,7-cholestadiene 24,25-ketals and alkanoyl derivatives thereof comprising the steps of halogenating 24R,25- and 24S,25-dihydroxycholesterol 24,25-ketals and alkanoyl derivatives thereof to 7-halo-24R,25- and 7-halo-24S,25-dihydroxycholesterol 24,25-ketals and alkanoyl derivatives thereof, dehydrohalogenating 7-halo-24R,25- and 7-halo-24S,25-dihydroxycholesterol 24,25-ketals and alkanoyl derivatives thereof to pure 3,24R,25- and 3,24S,25-trihydroxy-5,7-cholestadiene 24,25-ketals and alkanoyl derivatives thereof and hydrolyzing the alkanoyl function, if necessary.

The present invention also relates, more particularly, to a process for the preparation of 3,24R,25- and 3,24S,25-trihydroxy-5,7-cholestadiene 24,25-ketals thereof comprising the steps of halogenating 24R,25- and 24S,25-trihydroxy-cholesteryl 3,24-diacylate to 7-halo-24R,25- and 7-halo-24S,25-dihydroxycholesteryl 3,24-dicylate, dehydrohalogenating 7-halo-24-diacylate, 25- and 7-halo-24S,25-dihydroxycholesteryl 3,24-diacylate to pure 3,24R,25-and 3,24S,25-trihydroxy-5,7-cholestadiene 3,24-diacylate, hydrolyzing the alkanoyl functions and ketalizing 3,24R,25- and 3,24S,25-trihydroxy-5,7-cholestadiene to 3,24R,25- and 3,24S,25-trihydroxy-5,7-cholestadiene 24,25-ketals.

As used throughout the specification and the appended claims, the term "alkyl group" refers to a monovalent substituent consisting solely of carbon and hydrogen of from 1 to 20 carbon atoms which may be straight or branched-chain. Examples of alkyl groups are methyl, ethyl, n-propyl, i-propyl, tert-butyl, hexyl, octyl, and so forth. The term "alkylene group" refers to a divalent substituent consisting solely of carbon and hydrogen of from 1 to 20 carbon atoms which may be straight or branched-chain and whose free valences are attached to two distinct groups. Examples of alkylene groups are methylene, ethylene, propylene and so forth. The term "alkoxy group" refers to a monovalent substituent which consists of an alkyl group linked through an ether oxygen having its free valence bond from the ether oxygen. Examples of alkoxy groups are methoxy, ethoxy, isopropoxy, tert-butoxy and so forth. The term "phenyl alkoxy" refers to an alkoxy group which is substituted by a phenyl ring. Examples of phenyl alkoxy groups are benzyloxy, 2-phenylethoxy, 4-phenylbutoxy and so forth. The term "alkanoyloxy group" refers to the residue of an alkylcarboxylic acid formed by removal of the hydrogen from the hydroxyl portion of the carboxyl group. Examples of alkanoyloxy groups are formyloxy, acetoxy, butyryloxy, hexanoyloxy and so forth. The term "substituted" as applied to "phenyl" refers to phenyl which is substituted with one or more of the following groups: alkyl, halogen (i.e., fluorine, chlorine, bromine or iodine), nitro, cyano, trifluoromethyl and so forth. The term "lower" as applied to any of the aforementioned groups, refers to those groups having from 1 to 8 carbon atoms.

In the formulas presented herein, the various substitutents are illustrated as joined to the steroid nucleus by one of these notations: a solid line (—) indicating a substituent which is in the $\beta$-orientation (i.e., above the plane of the molecule), a dotted line ( - - - ) indicating a substituent which is in the $\alpha$-orientation (i.e., below the plane of the molecule), or a wavy line ( $\sim$ ) indicating a substituent which may be in the $\alpha$- or $\beta$-orientation. The formulas have all been drawn to show the compounds in their absolute stereochemical configurations. Since the starting materials are derived from naturally occurring stigmasterol, the products exist in the single absolute configuration depicted herein. However, the processes of the present invention are intended to apply as well to the synthesis of steroids of the "unnatural" and racemic series, i.e., the enantiomers of the compounds depicted herein and mixtures of both. Thus, one may begin the synthesis utilizing unnatural or racemic starting materials to prepare unnatural or racemic products, respectively. Optically active products can then be prepared by resolution of the racemic products utilizing in the preparation thereof standard resolution techniques well known in the steroid art.

The Greek letter xi ($\xi$) in the name of a vitamin $D_3$ intermediate or metabolite indicates that the stereochemistry of the substituent to which it refers is undefined or that the product consists of a mixture of compounds epimeric at the designated position.

The nomenclature adopted to define absolute configuration of substituents bound to carbon atom 24 of the steroid nucleus is described in the Journal of Organic Chemistry, 35, 2849 (1970) under the title "IUPAC Tentative Rules for the Nomenclature of Organic Chemistry. Section E. Fundamental Stereochemistry".

In the first step of the process of the present invention for the preparation of 3,24R,25- and 3,24S,25-trihydroxy-5,7-cholestadiene 24,25-ketals and alkanoyl derivatives thereof, 24R,25- or 24S,25-dihydroxycholesterol 24,25-ketal 3-acylate of the formula

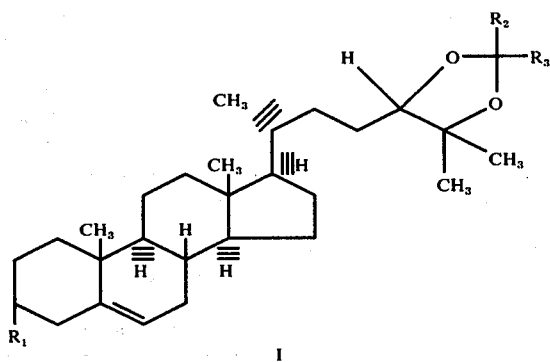

wherein
$R_1$ is alkanoyloxy, $R_2$ and $R_3$ each independently are lower alkyl, $R_2$ and $R_3$ taken together are lower alkylene and the absolute configuration at C-24 is R or S, the synthesis of which is described in U.S. Patent Application Ser. No. 664,833, filed Mar. 8, 1976, are allylically halogenated to a mixture of 7α- and 7β-halo-24R,25- or 24S,25-dihydroxycholesteryl 24,25-ketal 3-acylates of the formula

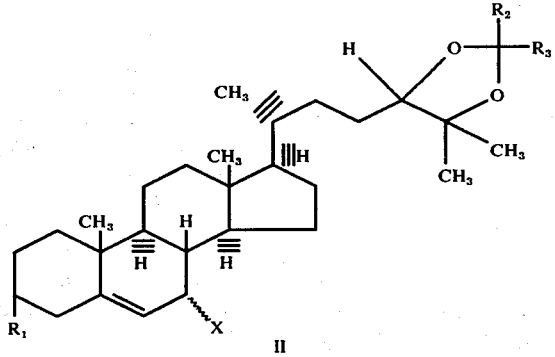

wherein
$R_1$, $R_2$ and $R_3$ are as above, X is bromo or chloro and the absolute configuration at C-24 is R or S.

The halogenation of 24R,25- and 24S,25-dihydroxycholesterol 24,25-ketal 3-acylates is accomplished using a suitable halogenating agent, such as 1,3-dibromo-5,5-dimethylhydantoin, N-chlorosuccinimide, N-chloroacetamide, N-bromosuccinimide, N-bromoacetamide and the like, dissolved in a saturated aliphatic hydrocarbon or halocarbon, such as hexane or carbon tetrachloride, in the presence of an acid scavenger, such as sodium bicarbonate or sodium carbonate at the boiling point of the reaction medium to give a mixture of the 7α- and 7β-halocholesterol ketal acylates, which is used in the following dehydrohalogenation step without separation of the 7β-halo-isomer from the predominant 7α-isomer.

The second and crucial step of the present process for the preparation of 3,24-R,25- and 3,24S,25-trihydroxy-5,7-cholestadiene 24,25-ketals and alkanoyl derivatives thereof involves the dehydrohalogenation of 7ξ-halo-24R,25- and 7ξ-halo-24S,25-dihydroxycholesteryl 24,25-ketal 3-acylates to a mixture of dienes of the formula

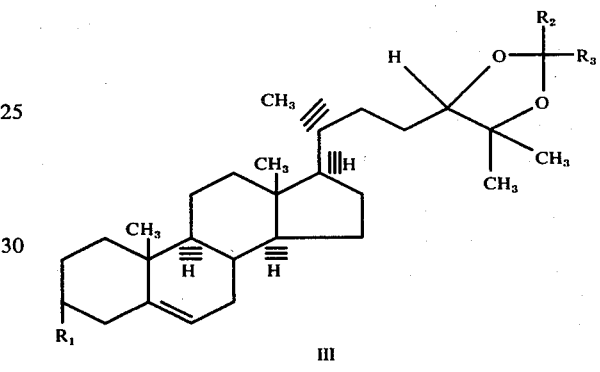

wherein
$R_1$, $R_2$ and $R_3$ are as above and the absolute configuration at C-24 is R or S and the formula

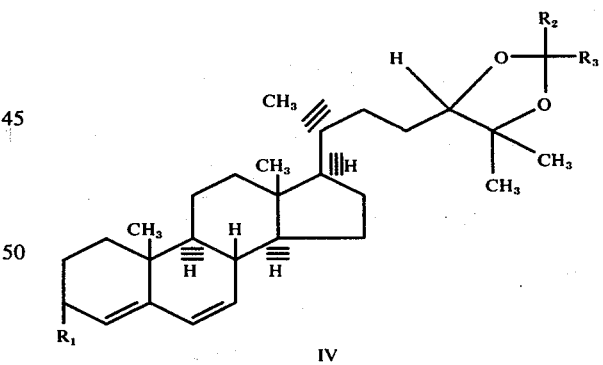

wherein
$R_1$, $R_2$ and $R_3$ are as above and the absolute configuration at C-24 is R or S which are difficultly separable and which in related systems according to DeLuca et al., Tetrahedron Letters, 4147 (1972) and Barton, et al., J.C.S. Chem. Comm., 203 (1974), require chromatography on silver nitrate-impregnated silica gel for isolation of the pure requisite 5,7-diene. Such chromatographic separations are costly and inefficient and, if possible, are to be avoided in a potential commercial process. It has now been found that the separation of the desired 5,7-diene of formula III from the minor undesired isomer of formula IV can be accomplished by the dehydroacyloxylation of the 3-acyloxy group of the 4,6-diene of formula IV to the 2,4,6-triene of the formula

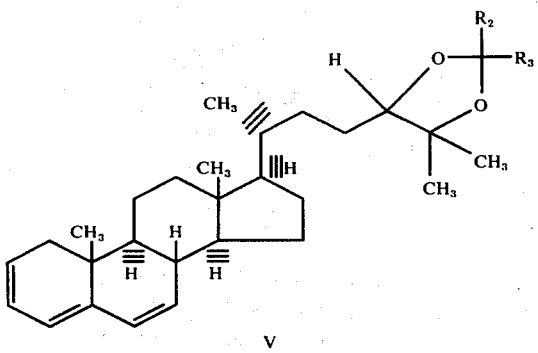

V wherein $R_2$ and $R_3$ are as above and the absolute configuration at C-24 is R or S followed by either direct crystallization of the diene-triene mixture of compounds III and V or by filtration of the mixture through a column of a suitable absorbent followed by crystallization. Suitable absorbents for the filtration include silica gel and neutral or basic alumina. This novel process for the separation of the diene mixture does not suffer from the disadvantages of related prior art processes. The instant process is rapid, inexpensive, efficient, convenient and, most importantly, adaptable to large scale commercial production.

The dehydrohalogenation of the crude mixture of 7α- and 7β-halodihydroxy-cholesteryl ketal acylates is effected by heteroaromatic and aliphatic tertiary amines in an inert organic solvent. Suitable heteroaromatic tertiary amines are pyridines and alkylated pyridines, such as picolines, lutidines and collidines; suitable aliphatic tertiary amines are triethylamine, tripropylamine, 1,5-diazabicyclo(4.3.0)non-5-ene, 1,4-diazabicyclo(2.2.2)octane and the like; s-collidine being preferred. Trialkylphosphites are also useful in the dehydrohalogenation step. Suitable inert organic solvents include aromatic and aliphatic organic solvents, such as benzene, toluene, xylene, decalin and the like. Xylene is the preferred solvent. The reaction proceeds readily at temperatures from about 50° C to the reflux temperature of the reaction medium, most readily at the reflux temperature of the solvent system. The mixture of 5,7- and 4,6-cholestadiene 24,25-ketal-3-acylates of formulas III and IV respectively, so obtained, without further purification, is then dissolved in an appropriate ethereal solvent, such as dioxane, tetrahydrofuran or acetone, acetone and dioxane being preferred, and is heated at from about 40° C to the boiling point of the reaction medium, 70° C being preferred, in the presence of a strong acid to give a mixture of 24R,25- or 24S,25-dihydroxy-2,4,6-cholestatriene 24,25-ketal of formula V wherein $R_2$ and $R_3$ are as hereinbefore defined and unchanged 3,24-R,25- or 3,24S,25-trihydroxy-5,7-cholestadiene 24,25-ketal 3-acylate, readily separable by either direct crystallization of the crude reaction product or filtration of the crude reaction product dissolved in a suitable organic solvent system, such as methanol and chloroform, 1.25% methanol in chloroform being preferred, through a column of a suitable absorbent, such as silica gel, followed by crystallization of the concentrated eluate in excellent yield.

Appropriate strong acids include sulfuric acid and those derived from sulfuric acid, such as methanesulfuric acid, ethanesulfonic acid, hexanesulfonic acid, benzenesulfonic acid, and p-toluenesulfonic acid. Methanesulfonic acid and p-toluenesulfonic acid are the preferred acidic dehydroacylating catalysts. p-Toluenesulfonic acid is particularly preferred.

The saponification of 24R,25- and 24S,25-dihydroxycholesta-5,7-diene 24,25-ketal 3-acylates of formula III wherein $R_1$ is lower alkanoyloxy to 24R,25- and 24S,25-dihydroxycholesta-5,7-diene 24,25-ketals of formula III wherein $R_1$ is hydrogen is conveniently conducted by methods well known in the art. For example, the saponification can be performed by dissolving the 3-acylate in an alcoholic solution of an alkali metal hydroxide and stirring the solution at a reduced temperature of from −20° to about +20°, a reduced temperature of about 0° C. being preferred. Suitable alcoholic solvents include methanol, ethanol, 2-propanol and the like. Suitable alkali metal hydroxides include sodium hydroxide and potassium hydroxide. Methanol and potassium hydroxide are preferred.

Alternately, 3,24R,25- and 3,24S,25-trihydroxy-5,7-cholestadiene 24,25-ketals and alkanoyl derivatives are prepared from 24R,25- and 24S,25-dihydroxycholesteryl 3,24-diacylates of the formula

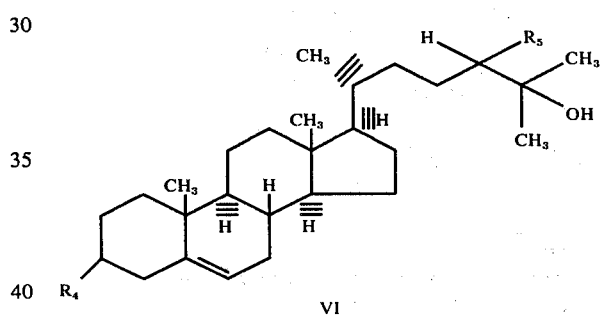

VI wherein $R_4$ and $R_5$ are lower alkanoyloxy and the absolute configuration at C-24 is R or S, the preparation of which is described in U.S. patent application Ser. No. 623,859, filed Oct. 20, 1975, by means of the halogenation-dehydrohalogenation, saponification sequence applied to the ketals of formula I, followed by ketalization.

For example, the diacylates of formula VI are allylically halogenated to a mixture of 7α- and 7β-halo-24R,25- or 24S,25-dihydroxycholesteryl 3,24-diacylates of the formula

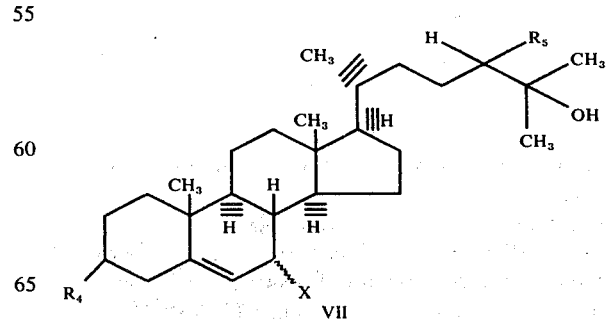

VII wherein $R_4$ and $R_5$ are as above, X is halo and the absolute configuration at C-24 is R or S which are dehydrohalogenated to 3,24R,25- or 3,24S,25-trihydroxy-5,7-cholestadiene 3,24-diacylates of the formula

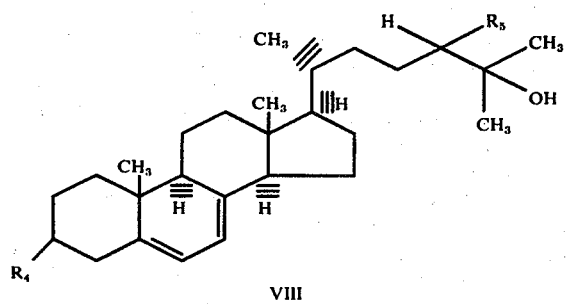

wherein
$R_4$ and $R_5$ are as above and the absolute configuration at C-24 is R or S and 3,24R,25- or 3,24S,25-trihydroxy-4,6-cholestadiene 3,24-diacylates of the formula

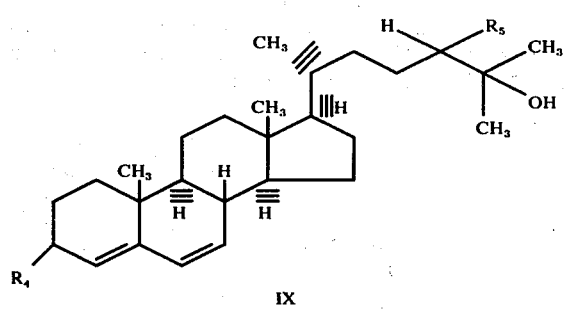

wherein
$R_4$ and $R_5$ are as above and the absolute configuration at C-24 is R or S.

Without purification, the mixture of dienes of formulas VIII and IX is selectively dehydroacyloxylated at the 3-position to a mixture of the diene of formula VIII and 24R,25- or 24S,25-dihydroxy-2,4,6-cholestatriene 24-acylates of the formula

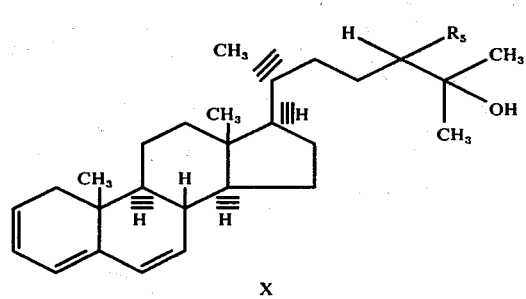

wherein
$R_5$ is as above and the absolute configuration at C-24 is R or S and the diene of formula VIII is isolated by either direct crystallization of the mixture or by filtration of the mixture through a column of a suitable absorbent.

The diene diacylate of formula VIII is saponified to 3,24R,25- or 3,24S,25-trihydroxy-5,7-cholestadiene of the formula

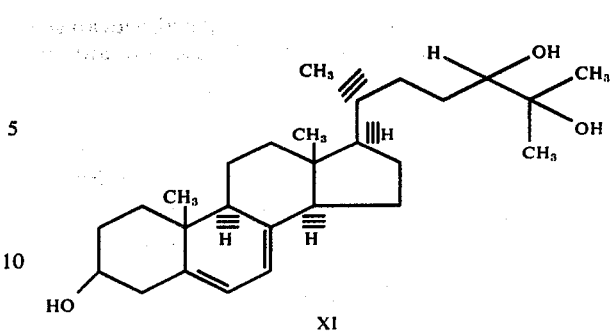

wherein
the absolute configuration at C-24 is R or S
which is then ketalized to compounds of formula I.

The ketalization is conveniently conducted by treating a compound of formula XI with a compound of the formula

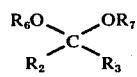

wherein
$R_2$ and $R_3$ are as above and $R_6$ and $R_7$ each taken independently are lower alkyl and $R_6$ and $R_7$ taken together are lower alkylene in the presence of an acid catalyst and an inert solvent.

As suitable acid catalysts there may be mentioned mineral acids such as hydrochloric acid, hydrobromic acid, sulfuric acid and the like; and organic sulfonic acids such as methanesulfonic acid, benzenesulfonic acid, para-toluenesulfonic acid and the like. Organic sulfonic acids are preferred. Para-toluenesulfonic acid is most preferred.

As suitable inert organic solvents there may be mentioned alkanols such as methanol, ethanol, 2-propanol and the like; and alkanones of the formula

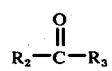

wherein
$R_2$ and $R_3$ are as above
such as acetone, 2-butanone, 3-pentanone, cyclohexanone and the like. It is preferred to employ the alkanone of formula XIII corresponding to the ketal of formula XII as the inert solvent. For example, when 3-penanone ketal is employed as the ketalyzing agent, it is preferred to employ 3-pentanone as the solvent. The combination of 2,2-dimethoxypropane and acetone is most preferred.

While the exchange ketalization reaction temperature is now narrowly critical, it is desirable to perform the reaction at reduced temperature to avoid undesirable side-reactions, such as dehydration of the hydroxyl groups. A reduced temperature of between about $-20°$ and $+20°$ is preferred. A reduced temperature of about $0°$ is most preferred.

The elimination-saponification steps may be reversed. For example, the mixture of compounds of formulas VIII and IX wherein $R_4$ and $R_5$ are alkanoyloxy may be first saponified to a mixture of carbinols of formulas VIII and IX wherein $R_4$ and $R_5$ are hydroxy and then selectively dehydrated to a mixture of dienes and trienes of formulas XI and X wherein $R_5$ is hydroxyl and the absolute configuration at C-24 is R or S, from which the diene XI may be separated by the aforementioned crystallization or filtration methods.

3,24R,25 and 3,24S,25-Trihydroxy-5,7-cholestadiene 24,25-ketals and the alkanoyl derivatives thereof are useful intermediates for the elaboration of the biologically important metabolite of vitamin $D_3$, 24R,25-dihydroxycholecalciferol and the unnatural 24S stereoisomer. The transformation of 3,24R,25- and 3,24S,25-trihydroxy-5,7-cholestadiene 24,25-ketals and 3-alkanoyl derivatives thereof to 24R,25- and 24S,25- dihydroxycholecalciferol is accomplished by photolysis to the previtamin followed by thermal isomerization of the previtamin and removal of the ketal and alkanoyl groups, if necessary. These transformations are described in U.S. patent application Ser. No. 664,799, filed Mar. 8, 1976.

The following examples are illustrative of the invention and are not to be construed as limiting the scope of the invention in any manner.

All temperatures are given in degrees Centigrade.

EXAMPLE 1

7-Bromo-24R,25-dihydroxycholesteryl 3,24-diacetate

A mixture of 7.59 g (0.0151 mol) of 24R,25-dihydroxycholesteryl 3,24-diacetate, 2.90 g (0.0098 mol) of 1,3-dibromo-5,5-dimethylhydantoin, 6.80 g of sodium bicarbonate and 300 ml of hexane was heated at reflux for 20 minutes. The solution was cooled and filtered free of solids and evaporated to dryness to yield 8.70 g (ca. 100%) of crude 7-bromo-24R,25-dihydroxycholesteryl 3,24-diacetate.

EXAMPLE 2

7-Bromo-24R,25-dihydroxycholesteryl 3-acetate 24,25-acetonide

A mixture of 0.500 g (0.0010 mole) of 24R,25-dihydroxycholesteryl 3-acetate 24,25-acetonide, 0.222 g (0.0075 mole) of 1,3-dibromo-5,5-dimethylhydantoin, 0.500 g of sodium bicarbonate and 50 ml of hexane was heated at reflux for 30 minutes. The solution was cooled and filtered free of solids and evaporated to dryness to yield 0.570 g of crude 7-bromo-24R, 25-dihydroxycholesteryl 3-acetate 24,25-acetonide.

EXAMPLE 3

7-Bromo-24S,25-dihydroxycholesteryl 3,24-diacetate

A mixture of 3.75 g (0.0075 mol) of 24S,25-dihydroxycholesteryl, 3,24-diacetate, 1.44 g of 1,3-dibromo-5,5-dimethylhydantoin, 3.77 g of sodium bicarbonate and 170 ml of hexane was heated at reflux for 20 minutes. The solution was cooled and filtered free of solids and evaporated to dryness to yield 4.35 g (ca. 100%) of crude 7-bromo-24S,25-dihydroxycholesteryl 3,24-diacetate.

EXAMPLE 4

7-Bromo-24S,25-dihydroxycholesteryl 3-acetate 24,25-acetonide

A mixture of 0.501 g (0.0010 mol) of 24S,25-dihydroxycholesteryl 3-acetate 24,25-acetonide, 0.222 g (0.0075 mol) of 1,3-dibromo-5,5-dimethylhydantoin, 0.500 g of sodium bicarbonate and 40 ml of hexane was heated at reflux for 30 minutes. The solution was cooled and filtered free of solids and evaporated to dryness to yield 0.577 g of crude 7-bromo-24S,25-dihydroxycholesteryl 3-acetate 24,25-acetonide.

EXAMPLE 5

3S,24R,25-Trihydroxy-5,7-cholestadiene 3,24-diacetate and 3S,24R,25-trihydroxy-4,6-cholestadiene 3,24-diacetate A mixture of 8.70 g (0.015 mol) of 7-bromo-24R,25-dihydroxycholesteryl 3,24-diacetate, 225 ml of xylene and 6.18 ml (0.047 mol) of s-collidine was heated at reflux for 1 hour. The cooled solution was diluted with 200 ml of benzene and washed with 125 ml of 1N hydrochloric acid and 125 ml of saturated aqueous sodium bicarbonate solution. The organic phase was then dried over anhydrous magnesium sulfate and concentrated to yield 7.60 g of a 65:35 mixture of 3S,24R,25-trihydroxy-5,7-cholestadiene 3,24-diacetate and 3S,24R,25-trihydroxy-4,6-cholestadiene 3,24-diacetate.

EXAMPLE 6

3S,24R,25-Trihydroxy-5,7-cholestadiene 3-acetate 24,25-acetonide and 24R,25-dihydroxy-2,4,6-cholestatriene 24,25-acetonide A mixture of 0.550 g (0.0095 mol) of 7-bromo-24R,25-dihydroxycholesteryl 3-acetate 24,25-acetonide, 25 ml of xylene and 0.60 ml (0.0045 mol) of s-collidine was heated at reflux for 1 hour. The cooled solution was diluted with 25 ml of benzene. This solution was washed with 2×10 ml of 1N hydrochloric acid and 2×10 ml of saturated aqueous sodium bicarbonate solution. The organic phase was dried over anhydrous magnesium sulfate, filtered, and evaporated to dryness to yield 0.470 g of a 65:35 mixture of 3S,24R,25-trihydroxy-5,7-cholestadiene 3-acetate 24,25acetonide and 3S,24R,25-trihydroxy-4,6-cholestadiene-3-acetate 24,25-acetonide.

This mixture was dissolved in 25 ml of acetone containing 0.2 g of p-toluenesulfonic acid monohydrate and this solution was heated at 60° C for 2 hours. The cooled solution was diluted with 25 ml of saturated aqueous sodium bicarbonate solution. This mixture was extracted with 3×25 ml of methylene chloride. The organic extracts were combined and dried over anhydrous magnesium sulfate. Removal of solvent and chromatography of the residue on silica gel afforded 0.282 g of 3S,24R,25-trihydroxy-5,7-cholestadiene 3-acetate 24,25-acetonide and 0.105 g of 24R,25-dihydroxy-2,4,6-cholestatriene 24,25-acetonide.

EXAMPLE 7

3S,24S,25-Trihydroxy-5,7-cholestadiene 3,24-diacetate and 3S,24S,25-trihydroxy-4,6-cholestadiene 3,24-diacetate A mixture of 4.35 g (0.0075 mol) of 7-bromo-24S,25-dihydroxycholesteryl 3,24-diacetate, 110 ml of xylene, and 3.08 ml (0.023 mol) of s-collidine was heated at reflux for 1 hour. The cooled solution was diluted with 120 ml of benzene and washed with 75 ml of 1N hydrochloric acid and 75 ml of saturated sodium bicarbonate solution. The organic phase was then dried over anhydrous magnesium sulfate and concentrated to yield 3.75 g of a 65:35 mixture of 3S,24S,25-trihydroxy-5,7-cholestadiene 3,24-diacetate and 3S,24S,25-trihydroxy-4,6-cholestadiene 3,24-diacetate.

EXAMPLE 8

3S,24S,25-Trihydroxy-5,7-cholestadiene 3-acetate 24,25-acetonide and 24S,25-dihydroxy-2,4,6-cholestatriene 24,25-acetonide A mixture of 0.577 g (0.0010 mol) of 7-bromo-24S,25-dihydroxycholesteryl 3-acetate 24,25-acetonide, 30 ml of xylene and 0.60 ml (0.0045 mol) of s-collidine was heated at reflux for 1 hour. The cooled solution was diluted with 30 ml of benzene. This solution was washed with 2×10 ml of 1N hydrochloric acid and 2×10 ml of saturated aqueous sodium bicarbonate solution. The organic phase was dried over anhydrous magnesium sulfate, filtered, and evaporated to dryness to yield 0.500 g of a 65:35 mixture of 3S,24S,25-trihydroxy-5,7-cholestadiene 3-acetate 24,25-acetonide, and 3S,24S,25-trihydroxy-4,6-cholestadiene 3-acetate 24,25-acetonide.

This mixture was dissolved in 25 ml of acetone containing 0.2 g of p-toluenesulfonic acid monohydrate and this solution was heated at 60° C for 2 hours. The cooled solution was diluted with 50 ml of saturated aqueous sodium bicarbonate solution and extracted with 3×25 ml of methylene chloride. The combined organic extracts were dried over anhydrous magnesium sulfate, filtered, and evaporated to dryness. The residue was chromatographed on silica gel affording 0.292 g of 3S,24S,25-trihydroxy-5,7-cholestadiene 3-acetate 24,25-acetonide and 0.110 g of 24S,25-dihydroxy-2,4,6-cholestatriene 24,25-acetonide.

EXAMPLE 9

3S,24R,25-Trihydroxy-5,7-cholestadiene and 24R,25-dihydroxy-2,4,6-cholestatriene A solution of the 65:35 mixture of 7.60 g (0.015 mol) of 3S,24R,25-trihydroxy-5,7-cholestadiene 3,24-diacetate and 3S,24R,25-trihydroxy-4,6-cholestadiene 3,24-diacetate, 60 ml of dioxane and 150 ml of 5% potassium hydroxide in methanol was stirred at 0° for 1 hour. A solution of 200 ml of cold 0.5N sulfuric acid was added and the mixture was extracted with 4 × 200 ml. of methylene chloride and 4 × 200 ml. of brine and dried over anhydrous magnesium sulfate. Removal of the solvent afforded 6.20 g. of a 65:35 mixture of 3S,24R,25-trihydroxy-5,7-cholestadiene and 3S,24R,25-trihydroxy-4,6-cholestadiene. This mixture was taken up in 200 ml. of dry dioxane containing 0.7 g. of p-toluenesulfonic acid monohydrate and this solution was heated at 70° for 1 hour. The cooled solution was diluted with 100 ml. of ice water and 50 ml. of saturated aqueous sodium bicarbonate solution. The solution was filtered to yield 3.43 g. of crude solid. Recrystallization from dimethylformamide-water yielded 2.30 g. (37%) of 3S,24R,25-trihydroxy-5,7-cholestadiene, m.p. 216°–219°.

$[\alpha]_D^{22}$ −78.8° ($c$,1.03, dimethylformamide).

The filtrate was extracted with 4 × 300 ml. of chloroform and the combined organic extracts were washed with 200 ml. of saturated brine and dried over anhydrous sodium sulfate. Removal of solvent and chromatography of the residue on silica gel afforded 2.14 g. (36%) of 24R,25-dihydroxy-2,4,6-cholestatriene and 0.15 g. (2%) of 3,24R,25-trihydroxy-5,7-cholestadiene, m.p. 216°–219°.

EXAMPLE 10

3S,24R,25-Trihydroxy-5,7-cholestadiene 24,25-acetonide

A mixture of 0.280 g (0.00056 mol) of 3S,24R,25-trihydroxy-5,7-cholestadiene 3-acetate 24,25-acetonide and 10 ml of 5% potassium hydroxide in methanol was stirred at 0° for 1 hour. The solution was diluted with 20 ml of water and this mixture was extracted with 3×20 ml of ethyl acetate. The combined organic layers were washed with 2×10 ml of water and 2×10 ml of saturated brine. The organic phase was dried over anhydrous magnesium sulfate, filtered, and evaporated to dryness. The residue was recrystallized from ethyl acetate to give 0.226 g of 3S,24R,25-trihydroxy-5,7-cholestadiene 24,25-acetonide, m.p. 176°–179°.

$[\alpha]_D^{25}$ −106.2° ($c$, 1.10, CHCl$_3$).

EXAMPLE 11

3S,24S,25-Trihydroxy-5,7-cholestadiene and 24S,25-dihydrox-2,4,6-cholestatriene

A solution of the 65:39 mixture of 3.75 g (0.0075 mol) of 3S,24S,25-trihydroxy-5,7-cholestadiene 3,24-diacetate and 3S,24S,25-trihydroxy-4,6-cholestadiene 3,24-diacetate, 30 ml of dioxane and 75 ml of 5% potassium hydroxide in methanol was stirred at 0° for 1 hour. A solution of 100 ml of cold 0.5N sulfuric acid was added and the mixture was extracted with 4×100 mol of ethyl acetate. The organic layers were washed with 2×100 ml of brine and dried over anhydrous magnesium sulfate.

Removal of solvent afforded 3.05 g. of a 65:35 mixture of 3S,24S,25-trihydroxy-5,7-cholestadiene and 3S,24S,25-trihydroxy-4,6-cholestadiene. This mixture was taken up in 100 ml. of dioxane containing 0.5 g. of p-toluenesulfonic acid monohydrate and this solution was heated at 70° for 1 hour. The cool solution was diluted with 50 ml. of ice water and 25 ml. of saturated sodium bicarbonate solution. The mixture was filtered to yield 1.76 g. of crude solid. Recrystallization from dimethylformamide yielded 1.25 g. (40%) of 3S,24S,25-trihydroxy-5,7-cholestadiene, m.p. 228°–230°.

$[\alpha]_D^{65}$ −102.6° ($c$, 1.02, dimethylformamide)

The filtrate was extracted with 3 × 200 ml. of ethyl acetate and the combined organic extracts were washed with 200 ml. of saturated brine and dried over anhydrous sodium sulfate. Removal of solvent and chromatography of the residue on silica gel afforded 1.06 g. (35%) of 24S,25-dihydroxy-2,4,6-cholestatriene and 0.10 g. (3%) of 3,24S,25-trihydroxy-5,7-cholestadiene, m.p. 228°–230°.

EXAMPLE 12

3S,24S,25-Trihydroxy-5,7-cholestadiene 24,25-acetonide

A mixture of 0.285 g (0.00057 mol) of 3S,24S,25-trihydroxy-5,7-cholestadiene 3-acetate 24,25-acetonide and 10 ml of 5% potassium hydroxide in methanol was stirred at 0° for 1 hour. The solution was diluted with 20 ml of water. This mixture was extracted with 3×20 ml of ethyl acetate and the combined organic layers were washed with 2×10 ml of water and 2×10 ml of saturated brine. The organic phase was dried over anhydrous magnesium sulfate, filtered, and evaporated to dryness. The residue was recrystallized from ethyl acetate to afford 0.230 g of 3S,24S,25-trihydroxy-5,7-cholestadiene 24,25-acetonide, mp 188°–190°.

$[\alpha]_D^{25}$ −96.0° (c, 1.18, CHCl$_3$).

EXAMPLE 13

3S,24R,25-Trihydroxy-5,7-cholestadiene 24,25-acetonide

A mixture of 2.10 g (0.00504 mol) of 3S,24R,25-trihydroxy-5,7-cholestadiene, 60 ml of 2,2-dimethoxypropane and 0.24 g of p-toluenesulfonic acid monohydrate was stirred at 25° for 15 minutes. A total of 60 ml of methanol was added and the solution was stirred for 45 minutes. The mixture was diluted with 20 ml of saturated aqueous sodium bicarbonate solution and 100 ml of water. The mixture was extracted with 4×100 ml of methylene chloride. The organic extracts were washed with 100 ml of water and dried over anhydrous sodium sulfate. Removal of solvent and recrystallization from ethyl acetate yielded 2.06 g. (90%) of 3S,24R,25-trihydroxy-5,7-cholestadiene 24,25-acetonide, m.p. 176°–179°.

$[\alpha]_D^{24}$ −105.8° (c, 1.01, CHCl$_3$)

EXAMPLE 14

3S,24S,25-Trihydroxy-5,7-cholestadiene 24,25-acetonide

A mixture of 1.79 g. (0.0043 mol) of 3S,24S,25-trihydroxy-5,7-cholestadiene, 50 ml. of 2,2-dimethoxypropane and 0.20 g. of p-toluenesulfonic acid monohydrate was stirred at 25° for 15 minutes. A total of 50 ml. of methanol was added and the solution was stirred for 45 minutes. The mixture was diluted with 20 ml. of saturated sodium bicarbonate solution and 100 ml. of water and this solution was extracted with 4 × 100 ml. of methylene chloride. The organic extracts were washed with 100 ml. of water and dried over anhydrous sodium sulfate. Removal of solvent and recrystallization from ethyl acetate yielded 1.76 g. (90%) of 3S,24S,25-trihydroxy-5,7-cholestadiene 24,25-acetonide, m.p. 188°–190°.

$[\alpha]_D^{25}$ −96.4° (c, 1.00, CHCl$_3$)

We claim:

1. A compound of the formula

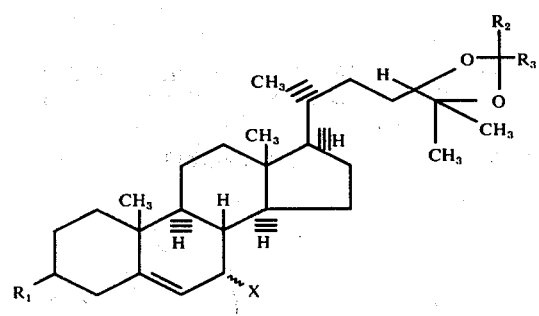

wherein
R$_1$ is hydroxy or lower alkanoyloxy, R$_2$ and R$_3$ each independently are lower alkyl, R$_2$ and R$_3$ taken together are lower alkylene, X is bromo or chloro and the absolute configuration at C-24 is R or S.

2. The compound of claim 1 wherein R$_1$ is lower alkanoyloxy and R$_2$ and R$_3$ each independently are lower alkyl.

3. The compound of claim 2 which is 7-bromo-24R,25-dihydroxycholesteryl 3-acetate 24,25-acetonide.

4. The compound of claim 2 which is 7-bromo-24S,25-dihydroxycholesteryl 3-acetate 24,25-acetonide.

5. A compound of the formula

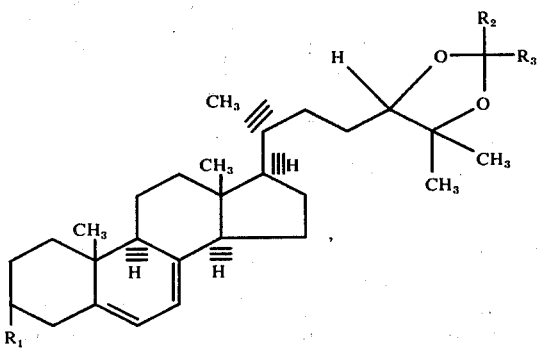

wherein
R$_1$ is hydroxy or lower alkanoyloxy, R$_2$ and R$_3$ each independently are lower alkyl, R$_2$ and R$_3$ taken together are lower alkylene and the absolute configuration at C-24 is R or S.

6. The compound of claim 5 wherein R$_1$ is hydroxy or lower alkanoyloxy and R$_2$ and R$_3$ each independently are lower alkyl.

7. The compound of claim 6 which is 3,24R,25-trihydroxy-5,7-cholestadiene 3-acetate 24,25-acetonide.

8. The compound of claim 6 which is 3,24S,25-trihydroxy-5,7-cholestadiene 3-acetate 24,25-acetonide, 9. The compound of claim 6 which is 3,24R,25-trihydroxy-5,7-cholestadiene 24,25-acetonide.

10. The compound of claim 6 which is 3,24S,25-trihydroxy-5,7-cholestadiene 24,25-acetonide.

11. A process for the preparation of 3,24,25-trihydroxy-5,7-cholestadiene 24,25-ketal and the alkanoyl derivative thereof of the formula

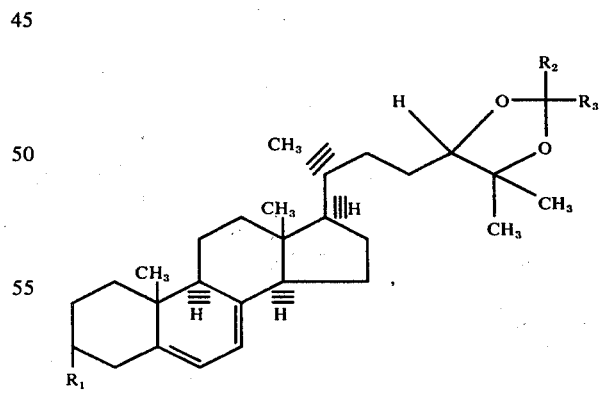

wherein
R$_1$ is hydroxy or lower alkanoyloxy, R$_2$ and R$_3$ each independently are lower alkyl, R$_2$ and R$_3$ taken together are lower alkylene and the absolute configuration at C-24 is R or S which comprises the steps of (a) treating a compound of the formula

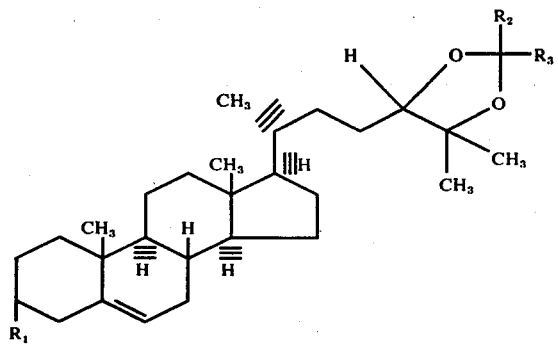

wherein
R₁, R₂ and R₃ are as above
with a chlorinating or brominating agent in an inert organic solvent to form a compound of the formula

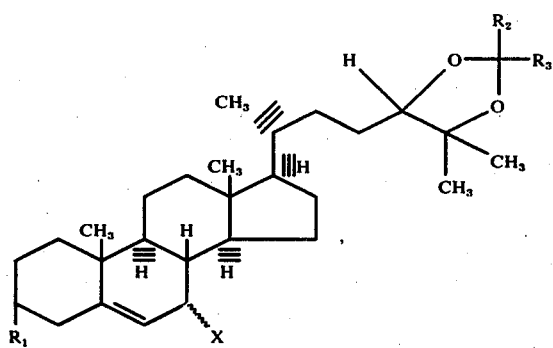

wherein
R₁, R₂ and R₃ are as above, X is chloro or bromo and the absolute configuration at C-24 is R or S (b) treating said product from step (a) with a heteroaromatic or aliphatic tertiary amine in an inert solvent to form a mixture of 3,24,25-trihydroxy-5,7-cholestadiene 24,25-ketal and the alkanoyl derivative thereof and a compound of the formula

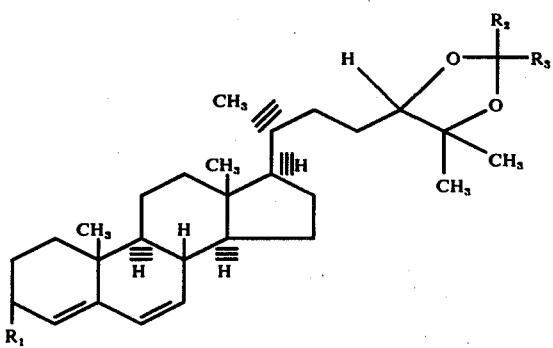

wherein
R₁, R₂ and R₃ are as above and the absolute configuration at C-24 is R or S (c) treating the mixture with an organic acid selected from the group consisting of sulfuric acid and sulfonic acids in a second inert organic solvent to form a second mixture of 3,24,25-trihydroxy-5,7-colestadiene 24,25-ketal and the alkanoyl derivative thereof and a compound of the formula

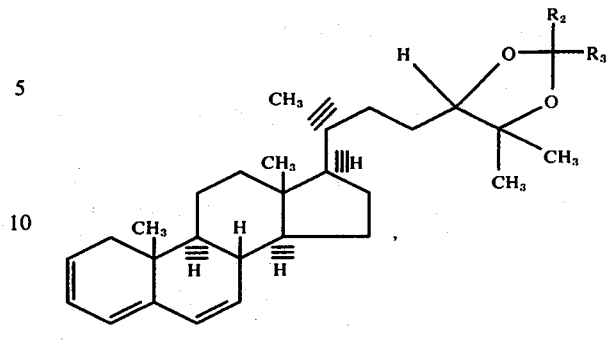

wherein
R₂ and R₃ are as above
and (d) separating the mixture to obtain pure 3,24,25-trihydroxy-5,7-cholestadiene 24,25-ketal and the alkanoyl derivative thereof.

12. The process of claim 11 wherein the heteroaromatic amine is an alkylpyridine.

13. The process of claim 12 wherein the alkylpyridine is s-collidine.

14. The process of claim 11 wherein the inert organic solvent is an aromatic solvent.

15. The process of claim 14 wherein the aromatic solvent is xylene.

16. A process for the preparation of a compound of the formula

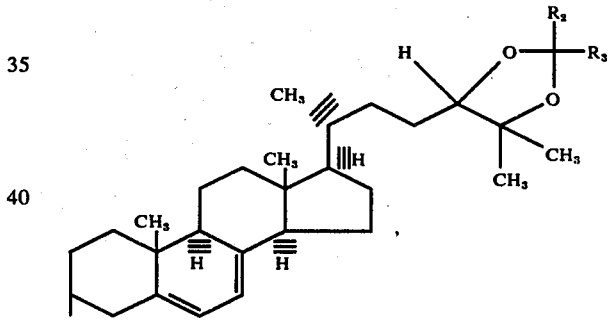

wherein
R₂ and R₃ each independently are lower alkyl, R₂ and R₃ taken together are lower alkylene and the absolute configuration at C-24 is R or S
which comprises treating a compound of the formula

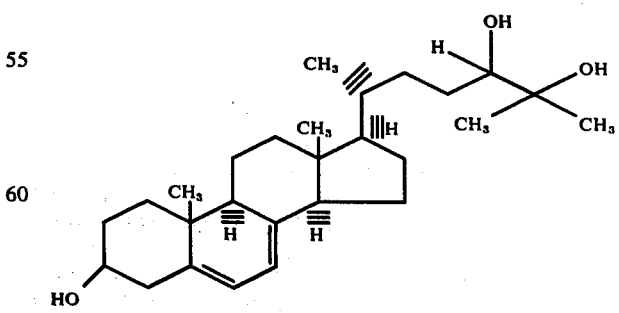

wherein
the absolute configuration at C-24 is R or S
with a compound of the formula

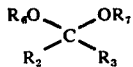

wherein
R$_2$ and R$_3$ are as above, R$_6$ and R$_7$ each independently are lower alkyl and R$_6$ and R$_7$ taken together are lower alkylene in the presence of a strong acid in an inert solvent at a reduced temperature.

17. The process of claim 16 wherein R$_2$ and R$_3$ each independently are lower alkyl.

18. The process of claim 16 wherein the strong acid is a sulfonic acid.

19. The process of claim 18 wherein the strong acid is para-toluenesulfonic acid.

20. The process of claim 16 wherein the inert solvent is an organic solvent.

21. The process of claim 20 wherein the organic solvent is acetone.

22. The process of claim 20 wherein the organic solvent is methanol.

23. The process of claim 16 wherein the reaction temperature is between about −20° C. and +20° C.

24. The process of claim 23 wherein the reaction temperature is about 0° C.

25. The process of claim 11 wherein the sulfonic acid is p-toluenesulfonic acid.

* * * * *